US00PP21564P2

(12) United States Plant Patent
Kent

(10) Patent No.: US PP21,564 P2
(45) Date of Patent: Dec. 7, 2010

(54) ***GUZMANIA* PLANT NAMED 'BRIMSTONE'**

(50) Latin Name: ***Guzmania* hybrid**
Varietal Denomination: Brimstone

(76) Inventor: Jeffrey Kent, P.O. Box 2166, Vista, CA (US) 92085-2166

( * ) Notice: Subject to any disclaimer, the term of this patent is extended or adjusted under 35 U.S.C. 154(b) by 0 days.

(21) Appl. No.: 12/460,357

(22) Filed: Jul. 18, 2009

(51) Int. Cl.
*A01H 5/00* (2006.01)

(52) U.S. Cl. ..... Plt./371

(58) Field of Classification Search ..... Plt./371
See application file for complete search history.

*Primary Examiner*—Kent L Bell

(57) ABSTRACT

A new and distinct *Guzmania* cultivar named 'Brimstone' is disclosed, characterized by a compact plant habit, and unique bright red bracts.

1 Drawing Sheet

Latin name of the genus and species: *Guzmania* hybrid.
Variety denomination: 'Brimstone'.

BACKGROUND OF THE INVENTION

The new cultivar is a product of a planned breeding program. The new variety originated from a cross pollination of the seed parent, of *Guzmania* hybrid 'Cutucu Hybrid,' unpatented with the unnamed pollen parent *Guzmania wittmackii*× *variegata,* unpatented, directed and performed by the inventor in February 1999. The cross was made at a commercial greenhouse in Vista, Calif.

'Brimstone' was discovered by the inventor, Jeffrey Kent, in December of 2002 at a commercial greenhouse in Vista, Calif. in a group of seedlings resulting from the 1999 crossing.

Asexual reproduction of the new cultivar 'Brimstone' was first performed at a commercial laboratory in Vista, Calif. by tissue culture in 2003. Since that time, approximately 6 generations have been reproduced by micro-propagation and has shown that the unique features of this cultivar are stable and reproduced true to type.

SUMMARY OF THE INVENTION

The cultivar 'Brimstone' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Brimstone' These characteristics in combination distinguish 'Brimstone' as a new and distinct *Guzmania* cultivar:

1. Very clear, bright inflorescence color.
2. Extension of bright color from inflorescence through scape.
3. Rapid growth.
4. Foliage tips remain healthy and intact, not showing the condition commercially known as "leaf tipping" typical of Guzmanias.

PARENTAL COMPARISON

Plants of the new cultivar 'Brimstone' are similar to the seed parent in most horticultural characteristics. However, 'Brimstone' differs from *Guzmania* hybrid 'Cutucu Hybrid' in having a brighter inflorescence color, taller plant height and much faster growth.

Plants of the new cultivar 'Brimstone' are similar to the pollen parent in most horticultural characteristics. However, 'Brimstone' differs from the unnamed *Guzmania wittmackii*× *variegata* in having a brighter inflorescence color, more compact plant habit, and much faster growth.

COMMERCIAL COMPARISON

'Brimstone' can be compared to the patented commercial variety *Guzmania* 'Deplakar', U.S. Plant Pat. No. 13,754. Plants of 'Deplakar' are similar to plants of 'Brimstone' in most horticultural characteristics, however, 'Brimstone' has shorter, narrow foliage, scape and terminal bracts more yellow than orange-yellow in color.

'Brimstone' can be compared to the unpatented commercial variety *Guzmania* 'Marjan' Plants of 'Marjan' are similar to plants of 'Brimstone' in most horticultural characteristics, however, 'Brimstone' has a wider inflorescence, and a shorter overall plant height than 'Marjan'.

BRIEF DESCRIPTION OF THE PHOTOGRAPH

Figure 1:
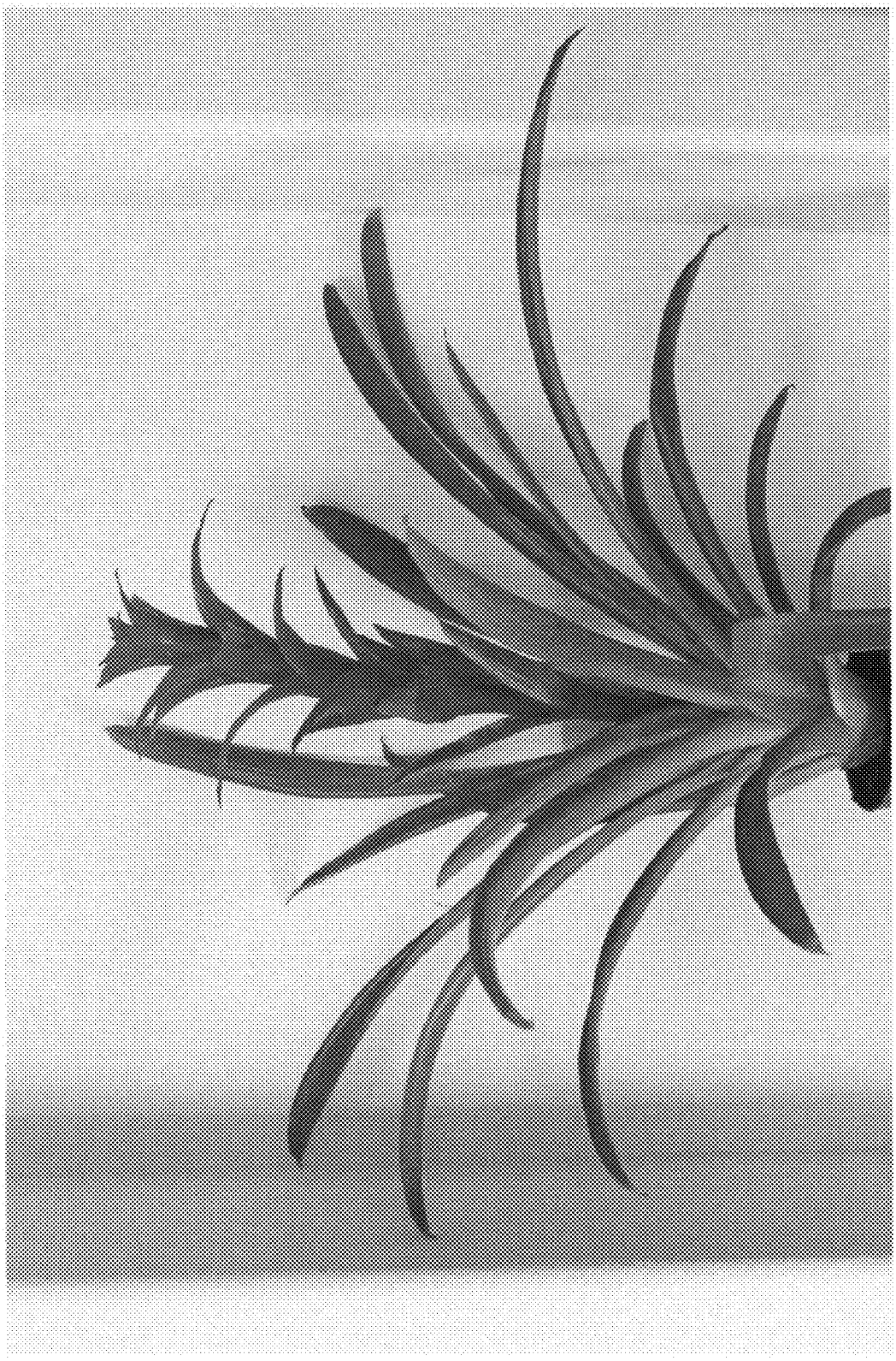
Figure 1:
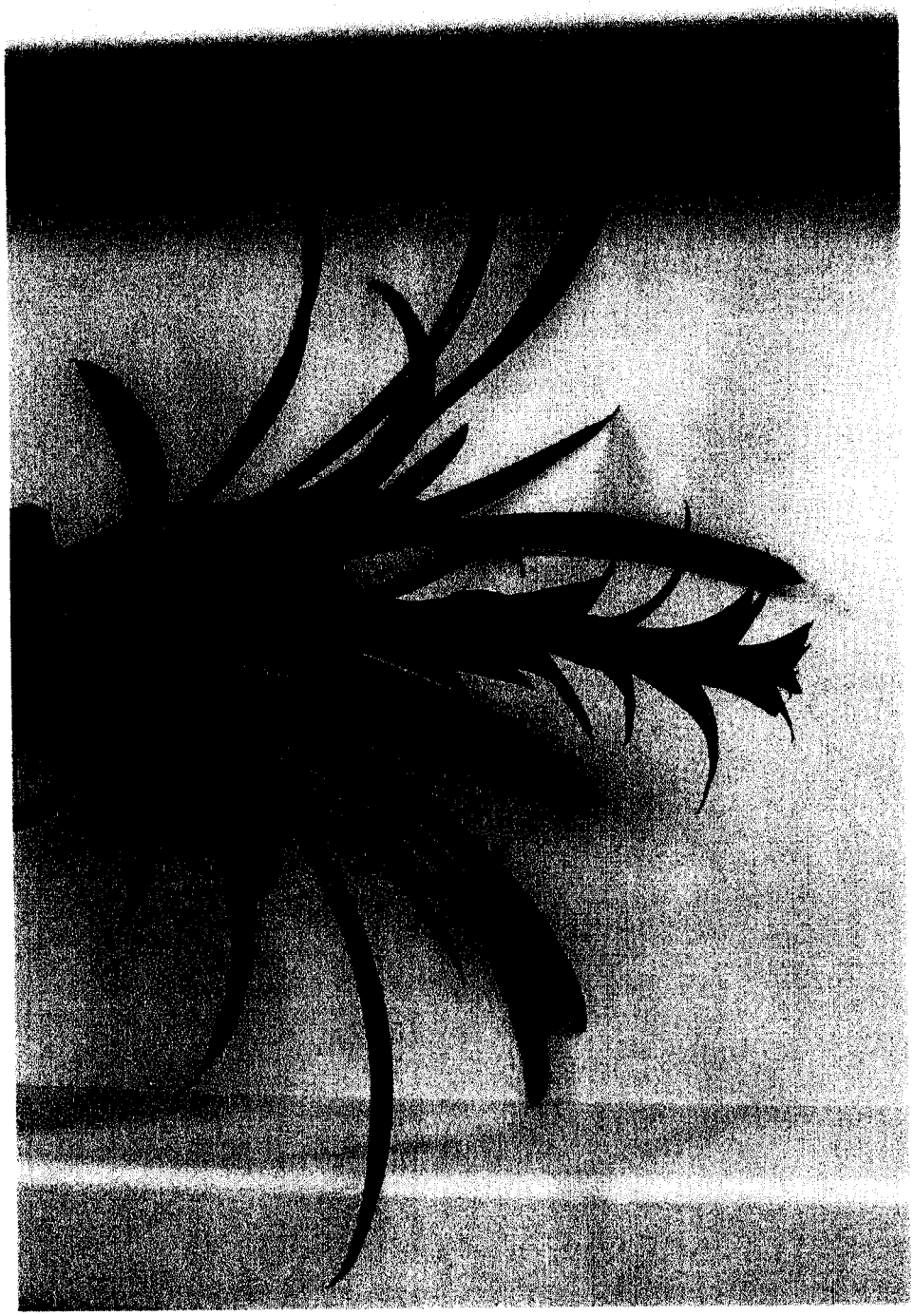

The accompanying photograph in FIG. 1 illustrates in full color a typical plant of 'Brimstone' grown in a greenhouse in Florida. This plant is approximately 2 years old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Brimstone' plants grown in a climate controlled greenhouse in Miami, Fla. Temperatures ranged from 20° C. to 28° C. night and day. No artificial light, photoperiodic treatments or chemical treatments were given to the plants. Measurements and numerical values represent averages of typical plant types.

Botanical classification: *Guzmania* hybrid cultivar 'Brimstone.'
Age of the plant described: Approximately 2 years.
Container size of the plant described: 6 inch.

PLANT

Growth habit: Upright, arching, forming compact rosettes around a single axis. Single, straight, upright inflorescence arising from the center of plant.
Height: Approximately 65 cm in a 6 inch pot, measured from the soil level of the pot.
Plant spread: Approximately 95 cm in a 6 inch pot.
Normal pot size: 6" and larger pots.
Growth rate: Rapid.
Branching characteristics: Upright, non-branching.
Number of leaves per stem: Approximately 25.
Stem length: Approximately 12 cm.
Stem width: Approximately 14 cm.
Stem color: Near RHS Yellow-Green 145A.
Stem texture: Smooth.
Age of plant described: Approximately 2 years.

FOLIAGE

Leaf:
*Arrangement.*—Whorled, single occurring basal rosettes.
*Average length.*—Approximately 55 cm.
*Average width.*—Approximately 4.5 cm.
*Shape of blade.*—Ligulate.
*Aspect.*—Recurved.
*Apex.*—Apiculate.
*Base.*—Sheathing. Sheath length: Average 7 cm. Sheath width: Average 9 cm. Sheath color: Near RHS Yellow-Green 145A. Margin: Entire.
*Texture of top surface.*—Smooth, slightly glossy.
*Texture of bottom surface.*—Smooth, slightly glossy.
*Color.*—Young foliage upper side: Near RHS Green 137B, base Yellow-Green 145C with flushing near Red-Purple 59C. Young foliage under side: Near RHS Green 137B, base Yellow-Green 145C with flushing near Red-Purple 59C. Mature foliage upper side: Near RHS Green 137B, base near Yellow-Green 145A. Mature foliage under side: Near RHS Green 137B, base near Yellow-Green 145A.
*Venation.*—Type: Parallel. Venation coloration: Indistinguishable from foliage coloration.
Petiole: Not present, sessile.

INFLORESCENCE

General description: Simple spike(scape) consisting of many bracts only. No individual flowers are visible. Spike emerges from the centre of the rosette. Inflorescence is formed by conspicuous bracts.
*Inflorescence height, excluding scape.*—Approximately 24 cm.
*Inflorescence width.*—Approximately 22 cm.
Scape:
*Length.*—Approximately 30 cm.
*Width.*—Approximately 3.5 cm.
*Aspect.*—Very straight, Approximately 90° angle to rosette.
*Strength.*—Very strong.
*Color.*—Near RHS Red 53C with blotches near Yellow-Green 145C.
Bracts:
*Scape/Lowermost Bracts.*—Shape: Ligulate. Length: Approximately 22 cm, excluding sheath. Width: Approximately 4.2 cm. Quantity: Average 6. Tip: Acute. Base: Sheathed. Sheath length: Approximately 5 cm. Sheath width: Approximately 4.5 cm. Sheath color: Near RHS Yellow-Green 145C with blotches near Red 53C. Margin: Entire. Color Upperside: Near RHS Red 53D, up to approximately ⅓ from base. ⅔ near apex, near RHS Green 137B. Color Underside: Near RHS Red 53D, up to approximately ⅓ from base. ⅔ near apex, near RHS Green 137B.
*Terminal bracts.*—Shape: Ligulate. Length: Approximately 9 cm, excluding sheath. Width: Approximately 3 cm. Quantity: Average 17 to 18. Tip: Acute. Base: Sheathed. Sheath length: Approximately 4 cm. Sheath width: Approximately 4 cm. Sheath color: Near RHS Red 53B. Margin: Entire. Coloration Terminal Bracts: Upperside: Near RHS Red 42A, tip near Greyed-Purple N186C. Underside: Near RHS Red 45C, tip near Greyed-Purple N186C.

OTHER CHARACTERISTICS

Disease Resistance: Neither resistance nor susceptibility to diseases or pests has been observed in this variety.
Drought Tolerance and Cold Tolerance: Observed to tolerate temperatures to 40° C. without any negative effects. Temperature tolerance above this range has not been observed. Tolerance of cold temperatures has not been observed.
Fruit/seed production: Not observed.

What is claimed is:

1. A new and distinct cultivar of *Guzmania* plant named 'Brimstone' as herein illustrated and described.

* * * * *

UNITED STATES PATENT AND TRADEMARK OFFICE

CERTIFICATE OF CORRECTION

PATENT NO. : PP21,564 P2
APPLICATION NO. : 12/460357
DATED : December 7, 2010
INVENTOR(S) : Jeffrey Kent It is certified that error appears in the above-identified patent and that said Letters Patent is hereby corrected as shown below:

The drawing included in the grant is incorrect. Please replace drawing with attached. The plant illustrated in the drawing issued with patent PP21564 is not from the drawing submitted by the applicant.

Signed and Sealed this
Nineteenth Day of April, 2011

David J. Kappos

David J. Kappos
*Director of the United States Patent and Trademark Office*